(12) United States Patent
Lin et al.

(10) Patent No.: US 8,940,939 B2
(45) Date of Patent: Jan. 27, 2015

(54) PROCESS OF OXIDIZING CYCLOHEXANE

(75) Inventors: Min Lin, Beijing (CN); Chunfeng Shi, Beijing (CN); Bin Zhu, Beijing (CN); Yingchun Ru, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 0 days.

(21) Appl. No.: 14/115,754

(22) PCT Filed: May 2, 2012

(86) PCT No.: PCT/CN2012/000578
§ 371 (c)(1),
(2), (4) Date: Nov. 14, 2013

(87) PCT Pub. No.: WO2012/149827
PCT Pub. Date: Nov. 8, 2012

(65) Prior Publication Data
US 2014/0088327 A1   Mar. 27, 2014

(30) Foreign Application Priority Data

May 5, 2011   (CN) .......................... 2011 1 0117354

(51) Int. Cl.
*C07C 45/28* (2006.01)
*C07C 27/16* (2006.01)
*C07C 29/48* (2006.01)

(52) U.S. Cl.
CPC ................ *C07C 27/16* (2013.01); *C07C 29/48* (2013.01); *C07C 45/28* (2013.01); *C07C 2101/14* (2013.01)
USPC ......................................... 568/342; 568/836

(58) Field of Classification Search
USPC ................................................ 568/342, 836
See application file for complete search history.

(56) References Cited

U.S. PATENT DOCUMENTS

| 6,475,465 B2 * | 11/2002 | Lin et al. ....................... 423/716 |
| 7,837,977 B2 | 11/2010 | Miller |
| 2005/0288532 A1 * | 12/2005 | Genger et al. ................ 568/357 |
| 2007/0059237 A1 | 3/2007 | Miller |

FOREIGN PATENT DOCUMENTS

| CN | 1301599 A | 7/2001 |
| CN | 1132699 C | 12/2003 |
| CN | 1678389 A | 10/2005 |
| CN | 101279959 A | 10/2008 |
| CN | 102079695 A | 6/2011 |
| CN | 102206147 A | 10/2011 |
| WO | WO 90/05126 A1 | 5/1990 |

OTHER PUBLICATIONS

Tao, et al., "Cyclohexane Oxidation Catalyzed by Titanium Silicalite (TS-1) with Hydrogen Peroxide" *Journal of Natural Gas Chemistry* (2001) pp. 295-307, vol. 10, No. 4.
International Search Report dated Aug. 16, 2012 issued in International Application No. PCT/CN2012/000578.
Extended European Search Report dated Aug. 18, 2014 received from related Application No. 12780008.4.

* cited by examiner

*Primary Examiner* — Sikarl Witherspoon
(74) *Attorney, Agent, or Firm* — Scully, Scott, Murphy & Presser, P.C.

(57) ABSTRACT

A process of oxidizing cyclohexane, comprising feeding cyclohexane, an aqueous hydrogen peroxide solution and optionally an organic solvent into a reaction zone through a feed inlet thereof under the oxidation reaction conditions for contact, and providing all or most of the oxidation product at the reaction zone bottom, wherein a part or all of the packing in the reaction zone is a titanium silicate molecular sieve-containing catalyst. The process of oxidizing cyclohexane according to the present invention carries out the oxidation in the reaction zone, which, firstly, utilizes the latent heat from reaction sufficiently so as to achieve energy-saving; secondly, increases the yield of target product and the availability of oxidizer; and thirdly, allows the separation of the oxidation product from the raw material cyclohexane as the reaction proceeds, such that the cost for subsequent separations can be saved.

18 Claims, 1 Drawing Sheet

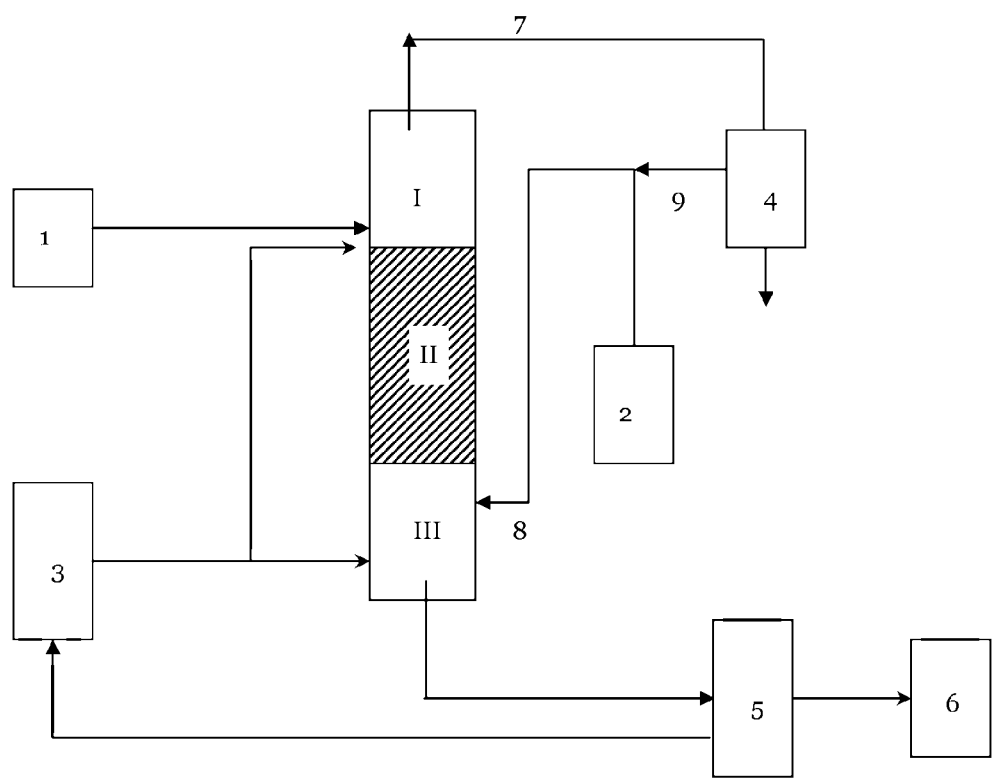

PROCESS OF OXIDIZING CYCLOHEXANE

TECHNICAL FIELD

The present invention relates to a process of epoxidising olefin.

BACKGROUND

Cyclohexanone and cyclohexanol, as important industrial chemicals, are widely used in the fields of fiber, synthetic rubber, industrial paint, medicine, pesticide, organic solvent and so on. As the rapid development of polyamide industry, the global quantity demanded for cyclohexanone and cyclohexanol, which serve as intermediates to produce Nylon 6 and Nylon 66, is greater than 2 million Tons.

Regarding the demand above, the skilled persons are devoted to developing processes of producing cyclohexanone (cyclohexanol) with high efficiency without pollution. The skilled persons deem that the oxidation of cyclohexane using hydrogen peroxide as an oxidizer and using titanium silicate molecular sieve as a catalyst to prepare cyclohexanone (cyclohexanol) satisfies the requirement of green chemistry and the developing idea of atom economy, and thus is a new green technology with great prospect to produce cyclohexane.

A plurality of factors affect the reaction of oxidizing cyclohexane catalyzed by the titanium silicate molecular sieve, such as the properties of the titanium silicate molecular sieve per se, the properties of the oxidizer hydrogen peroxide ($H_2O_2$), the selection of solvent, reaction conditions (e.g. temperature, feeding ratios, reaction pressure and the like) and so on. In order to increase the selectivity to cyclohexanone in the cyclohexane oxidation process, the skilled persons focus mainly on developing more effective titanium silicate molecular sieve catalyst, and optimizing the reaction conditions in the process to achieve the target above.

Although there are currently kinds of research on the reaction of oxidizing cyclohexane catalyzed by titanium silicate molecular sieve, most of them are restricted in laboratories, but are unavailable for a continuously industrial production. The defects of the existing processes lie in either the picky requirement on the devices or the high energy consumption, low yield and the like.

Therefore, how to develop a process for the reaction of oxidizing cyclohexane catalyzed by titanium silicate molecular sieve useful for commercially continuous production represents the main direction to which the research on the oxidation reaction of cyclohexane with a titanium silicate molecular sieve/$H_2O_2$ system is focused.

SUMMARY OF THE INVENTION

The purpose of the present invention is to provide a process for the continuous oxidation of cyclohexane useful for industrial application.

Currently, for the oxidation reaction of cyclohexane with a titanium silicate molecular sieve/$H_2O_2$ system, the use of solvent is essential. The addition of an appropriate solvent can allow the effective reaction, and can increase the selectivity to the target product. However, in view of the existing researches, in the oxidation reaction of cyclohexane with a titanium silicate molecular sieve/$H_2O_2$ system, the solvent is generally used in an amount of about 30-about 90 wt %, based on the total weight of the reaction liquor. So, the addition of solvent achieves the effective reaction, though the great amount thereof increases in turn the difficulty and cost of the subsequent separation, such that the potential for industrial application thereof is decreased. Moreover, the reaction is intensively exothermic, which needs energy consumption for cooling the reaction, while the separation of target product needs in turn energy consumption for heating. So, how to save energy consumption required or to use effectively the heat generated from the system is also a problem to be solved and being studied.

The present inventors attempt to provide a process for carrying out the reaction continuously, which can achieve a more effective separation and can further use the reaction heat from the system so as to save energy consumption. The present invention is thus achieved based on such conception.

In order to achieve the purpose above, the present invention provides a process of oxidizing cyclohexane, comprising feeding cyclohexane, an aqueous hydrogen peroxide solution and optionally an organic solvent into a reaction zone through the feed inlet under the oxidation reaction conditions for contact, providing all or most of the oxidation product at the column bottom of the reaction zone, and discharging the unreacted cyclohexane and a part of water from the reaction zone top. In one embodiment, the cyclohexane and water are discharged preferably in the form of an azeotrope from the reaction zone top. A part or all of the packing within the reaction zone is a catalyst containing titanium silicate molecular sieve. In one embodiment, the oxidation product comprises or is selected from the group consisting of cyclohexanone and/or cyclohexanol.

The process of oxidizing cyclohexane according to the present invention carries out the oxidation in the reaction zone (under the rectification conditions), which utilizes the latent heat from reaction sufficiently so as to achieve energy-saving. In addition, the present invention carrying out the oxidation reaction of cyclohexane in the reaction zone allows the separation of the oxidation product from the raw material cyclohexane as the reaction proceeds, such that the cost for subsequent separations can be saved. Moreover, the separation of product in the system facilitates the reaction toward the positive direction, so as to increase the yield of target product and the availability of oxidizer.

DESCRIPTION OF DRAWINGS

FIG. 1 exemplifies a device for carrying out the process of oxidizing cyclohexane according to the present invention.

EMBODIMENTS

The present invention provides a process of oxidizing cyclohexane, comprising feeding cyclohexane, an aqueous hydrogen peroxide solution and optionally an organic solvent into a reaction zone through the feed inlet under the oxidation reaction conditions for contact, and providing all or most of the oxidation product at the reaction zone bottom, wherein a part or all of the packing in the reaction zone is a titanium silicate molecular sieve-containing catalyst.

The present invention does not set any special limitation on the method of feeding cyclohexane, an aqueous hydrogen peroxide solution and optionally organic solvent through the feed inlet for the contact in the reaction zone. However, in order to allow a more sufficient contact of reactants in the reaction zone so as to complete the reaction as far as possible, the method of feeding cyclohexane, an aqueous hydrogen peroxide solution and optionally organic solvent into the reaction zone through the feed inlet comprises preferably: feeding the aqueous hydrogen peroxide solution and optionally the organic solvent into the reaction zone through a first feed inlet, and feeding the cyclohexane into the reaction zone through a second feed inlet. In the inventive process, the plate number or the theoretical plate number between the first feed inlet and the column bottom is of about 50%-about 100% of the total plate number or the total theoretical plate number in the reaction zone, more preferably of about 80%-about 100%. The plate number or the theoretical plate number between the second feed inlet and the column bottom is of about 10%-about 80% of the total plate number or the total theoretical plate number in the reaction zone, more preferably of about 30%-about 70%.

The present invention does not set any special limitation on the titanium silicate molecular sieve catalyst, which can be various shaped titanium silicate molecular sieve catalysts useful for the reaction zone. Preferably, the titanium silicate molecular sieve-containing catalyst comprises a carrier and the titanium silicate molecular sieve. The carrier is used in an amount of about 1-about 90 wt %, and the titanium silicate molecular sieve is used in an amount of about 10-about 99 wt %, based on the total weight of the catalyst.

The present invention does not set any special limitation on the carrier of the titanium silicate molecular sieve-containing catalyst, which can be various conventional carriers for a shaped catalyst, such as a heat-resistant porous inorganic oxide and/or silicate, specifically one or more of alumina, silica, titania, magnesia, zirconia, thoria, beryllia and clay. More preferably, the carrier is one or more of alumina, silica, magnesia and zirconia.

According to the present invention, the method of shaping the titanium silicate molecular sieve catalyst can be carried out using the known technology from prior art, comprising principally the steps of pulping, granulating, calcinating and the like, on which the present invention does not set any special limitation.

All the catalysts aforementioned can satisfy the requirement by the present invention; however, in order to overcome the phenomena of the tendency of the bed in the reaction zone to be collapsed, the tendency of abrasion or breaking of the catalyst and the like, and in order to obtain higher selectivity to and yield of the target product, the titanium silicate molecular sieve catalyst is preferably in the form of microsphere, having a diameter of about 2-about 5000 microns, preferably about 5-about 2000 microns. More preferably, the titanium silicate molecular sieve catalyst is prepared by a process comprising the steps of: hydrolyzing an organic silicon compound and an templating agent useful for producing the titanium molecular sieve under hydrolysis conditions to obtain a colloidal solution; then mixing homogeneously the titanium silicate molecular sieve and the colloidal solution to obtain a slurry; and granulating the slurry to obtain the catalyst in the form of microsphere.

Any catalyst obtained according to the preparation process above can be used to achieve the purpose according to the present invention; however, in order to provide the catalyst stronger ability to resist breaking, and to provide higher selectivity to and yield of the product, the mass ratio among the titanium silicate molecular sieve, the organic silicon compound, the templating agent useful for producing the titanium silicate molecular sieve and water is about 100:about 10-about 2000:about 2-40:about 50-about 1000, preferably about 100:about 100-about 500:about 5-about 40:about 50-about 500. More preferably, the conditions for hydrolysis comprise hydrolysis time of about 0.5-about 10 h, hydrolysis temperature of from room temperature to about 100 degrees C.

According to the present invention, the organic silicon compound can be various hydrolyzable organic silicon compounds, such as one or more of tetraethyl silicate, tetramethyl silicate, tetrapropyl silicate and tetrabutyl silicate, preferably tetraethyl silicate.

According to the present invention, the templating agent useful for producing the titanium silicate molecular sieve can be conventional various templating agents useful for producing the titanium silicate molecular sieve from prior art, such as tetrapropyl ammonium hydroxide, tetrapropyl ammonium bromide, tetrapropyl ammonium chloride and/or tetraethyl ammonium hydroxide and the like.

According to the present invention, particularly preferably, the templating agent useful for producing the titanium silicate molecular sieve is tetrapropyl ammonium hydroxide, and the organic silicon compound is tetraethyl silicate, such that the molecular sieve obtained thereby is particularly useful for the present invention.

For example, the process of preparing the titanium silicate molecular sieve catalyst according to the present invention can comprise preferably the steps of:

(1) under the conditions of an atmospheric pressure and a temperature of from room temperature to about 100 degrees C., adding an organic silicon compound into an aqueous solution for mixing, stirring and hydrolyzing for about 0.5-about 10 h to obtain a colloidal solution;

(2) adding a titanium silicate molecular sieve into the colloidal solution obtained in step (1), and mixing homogeneously to obtain a slurry, wherein the mass ratio among the titanium silicate molecular sieve, the organic silicon compound, the templating agent useful for producing the titanium silicate molecular sieve and water is about 100:about 10-about 2000:about 2-about 40:about 50-about 1000; and (3) after stirring the slurry above continuously for a period (generally about 0.5-about 5 h), a conventional spray granulation or balling granulation followed by calcination providing the catalyst in the form of microsphere.

The conditions for calcination according to the present invention can be the conventional calcination conditions which are known by those skilled in the art, and comprise generally calcinating at a temperature of from about 350 to about 600 degrees C. in an air atmosphere for about 0.5-about 12 h.

The inventor of the present invention finds out unexpectedly during the research that, according to the process of the present invention, when the titanium silicate molecular sieve catalyst is prepared according to the process above, the effective utility of hydrogen peroxide as an oxidizer can be further increased greatly.

According to the present invention, the titanium silicate molecular sieve in the titanium silicate molecular sieve catalyst can be a conventional titanium silicate molecular sieve. The titanium silicate molecular sieve can be either modified or unmodified, preferably at least one of a titanium silicate molecular sieve having the MFI structure (e.g. TS-1), a titanium silicate molecular sieve having the MEL structure (e.g. TS-2), and a titanium silicate molecular sieve having the BEA structure (e.g. Ti-β). More preferably, the titanium silicate molecular sieve has a structural formula of $xTiO_2 \cdot SiO_2$, wherein x is about 0.0001-about 0.04, preferably about 0.01-about 0.03, more preferably about 0.015-about 0.025.

In accordance with the present invention, the titanium silicate molecular sieve can be commercially available, or can be prepared. The process for preparing the titanium silicate molecular sieve is known to those skilled in the art. For example, the titanium silicate molecular sieve can be prepared by referring to the process described by [Journal of Natural Gas Chemistry 2001, 10(4): 295-307], or can be prepared by referring to the process for preparing catalyst disclosed by CN 101279959A.

More preferably, the titanium silicate molecular sieve in the titanium silicate molecular sieve catalyst has the MFI structure, and the crystal grain of the titanium silicate molecular sieve has a hollow structure. The cavity portion of the hollow structure has a radial length of about 5-about 300 nm. The adsorption capacity of benzene measured for the titanium silicate molecular sieve under the conditions of 25° C., $P/P_0=0.10$ and 1 h of adsorption time is at least 70 mg/g. There is a hysteresis loop between the adsorption isotherm and desorption isotherm for the nitrogen adsorption at low temperature of the molecular sieve A titanium silicate molecular sieve having the structure and properties above is generally called as a hollow titanium silicate molecular sieve, and the relevant parameters and the preparation process thereof can refer to CN1301599A.

According to the present invention, the amount of the titanium silicate molecular sieve catalyst contained in the packing can vary within a wide range; however, if the amount of the catalyst is too high, a too rapid reaction may be resulted, such that the subsequent separation may be difficult; while if the amount of the catalyst is too low, a too slow reaction may be resulted, such that the commercial industrialization thereof may be unfavorable. So, it is preferred that the packing contains about 30-about 100 wt %, more preferably about 30-about 70 wt %, of the titanium silicate molecular sieve-containing catalyst.

The packing containing the titanium silicate molecular sieve catalyst according to the present invention is preferably a mixed packing obtained from mixing homogeneously a conventional packing and the titanium silicate molecular sieve catalyst. In the present invention, the conventional packing can be various conventional packing usually used for a reaction zone, such as one or more of a Raschig ring, a Pall ring, a cascade ring, a Berl saddle, an Intalox saddle, and a metal Intalox saddle, specifically for example a θ ring, a β ring packing and the like.

It is known that in a catalytically oxidizing system of titanium silicate molecular sieve/$H_2O_2$, the main function of the solvent is to facilitate the reaction liquor to be a homogeneous phase. Following such a principle, the solvent should avoid a too high steric hindrance, so as to ensure the effective reaction. With regard to the selection of the solvent, those skilled in the art can make selection based on the principle above. Generally, an organic solvent can be used. However, the selection will not be restricted only by the requirement above, and should be selected pursuant to the specific oxidation reaction system. The inventor of the present invention finds out that in the system of oxidizing cyclohexane, any solvent system satisfying the requirement above can convert cyclohexane to the target product with relatively good effect, whilst the conversion of cyclohexane and the yield of the target product may be still limited. The inventor of the present invention further finds out that a better reaction effect can be obtained using one or more of alcohol, ketone and nitrile as the solvent, more preferably one or more of a $C_1$-$C_8$ alcohol solvent, a $C_3$-$C_8$ ketone solvent and a $C_2$-$C_8$ nitrile solvent, further preferably one or more of a $C_1$-$C_6$ alcohol solvent, a $C_3$-$C_6$ ketone solvent and a $C_2$-$C_7$ nitrile solvent. Among others, the alcohol can be an organic alcohol solvent, such as one or more of methanol, ethanol, n-propanol, isopropanol, t-butanol and isobutanol and the like. The ketone can be an organic ketone solvent, such as one or more of acetone, butanone and the like. The nitrile solvent can be one or more of acetonitrile, propionitrile, benzyl cyanide and the like. More preferably, the solvent is one or more of acetone, methanol, benzyl cyanide and tert-butanol. The solvent is such selected that it can be discharged from the reaction zone bottom together with the target products of cyclohexanone and/or cyclohexanol, and the like.

In addition, in one embodiment, the conventional organic solvent may be avoided; and alternatively, in one preferred embodiment, water can be used as the solvent. The water used as the solvent may be, for example, that contained in the aqueous hydrogen peroxide solution added as a raw material, and/or water separately added, and/or water generated from the reaction.

The present invention does not set any special limitation on the conditions for the oxidation reaction, as long as the purpose of the present invention can be achieved. Preferably, the conditions for the oxidation reaction comprise a temperature of about 40-about 200 degrees C., preferably about 60-about 180 degrees C.; and a reflux ratio of not less than about 2:1, preferably not less than about 4:1.

According to the present invention, the reaction temperature within the reaction zone is provided by a heating medium. According to the known knowledge in the art, it is very easy for those skilled in the art to understand that regarding the present invention, the preferred heating medium is cyclohexane or the solvent specifically used during the oxidation reaction. With regard to the specific selection of heating medium for the reaction, either the solvent or cyclohexane to be used as the specific heating medium can be generally determined by comparing the boiling points difference between the solvent used and the oxidation product with the boiling points difference between cyclohexane and the oxidation product. For example, when acetone is used as the solvent, the boiling points difference between acetone and the oxidation product is significantly greater than the boiling points difference between cyclohexane and the oxidation product, such that selecting acetone solvent as the heating medium will be superior obviously to selecting cyclohexane as the heating medium, so as to facilitate the subsequent separation easier. Of course, the boiling points difference is just one of the bases for selection, while in specific industrial processes, the selection will be made according to the specific requirements.

According to the present invention, the reaction zone bottom can comprise the heating medium, the solvent and/or other substances in addition to all or most of the oxidation product. This can be understood by those skilled in the art easily based on the ordinary skill, and thus will not be discussed in more detail here.

The present invention does not set any special limitation on the total plate number or the total theoretical plate number within the reaction zone, which is, however, preferably 20-45, more preferably 30-40.

The present invention does not set any special limitation on the mass ratio among cyclohexane, hydrogen peroxide and optionally the organic solvent. Generally, the mass ratio can be selected referring to the ratios among the various substances in the conventional system using the titanium silicate molecular sieve to catalytically oxidize cyclohexane, which can be further modified corresponding to the target product desired and the technical purpose to be achieved. Preferably, in the case of using an organic solvent, the mass ratio among cyclohexane, hydrogen peroxide and the organic solvent in the reaction feed is about 1:about 0.01-about 10:about 0.5-about 50, preferably about 1:about 0.03-about 2:about 3-about 15.

The present invention does not set any special limitation on the concentration of the aqueous hydrogen peroxide solution, which can be of about 20-about 80 wt % of hydrogen peroxide, such as the commercially available aqueous hydrogen peroxide solution with a concentration of about 27.5 wt %, about 30 wt %, or about 50 wt %. However, the addition of water may function adversely to the reaction, so, the use of an aqueous hydrogen peroxide solution having a mass concentration of the hydrogen peroxide as high as possible is preferable. Most of the commercially available aqueous hydrogen peroxide solutions generally have a concentration of 27.5 wt % or 50 wt %, accordingly the present invention can also be generally carried out and achieved by using these two aqueous hydrogen peroxide solutions. In one embodiment, the water contained in the aqueous hydrogen peroxide solution can be used as the solvent.

In order to simplify the subsequent separation step and to decrease the energy consumption of the device, it is generally preferable that, during the reaction, the raw materials react completely as far as possible within the reaction zone, such that the subsequent separation of the raw material hydrogen peroxide can be avoided. Therefore, the ratio of cyclohexane to hydrogen peroxide is particularly preferred to be about 1:about 1-about 2.

According to the present invention, in order to prevent collapse of the packing bed of the titanium silicate molecular sieve-containing catalyst within the reaction zone and to obtain better product yield, during the practical reaction process, the reaction zone can be divided into multi-stages pursuant to specific situations. The each stage can be separated from one another with conventional packing directly, wherein the thickness of the packing between the stages can be selected pursuant to the height of the each separated stage of the reaction zone, which is generally about 5-about 20 cm, preferably about 8-about 15 cm.

The present invention also provides a device capable of carrying out the process above, as showed by FIG. 1. The various parts of the device as well as the process according to the present invention carried out in the device can be illustrated as follows: hydrogen peroxide is fed through the reaction zone top I into the reaction zone from a stock tank 1. When a solvent is used, the solvent is fed through the top I and/or bottom III into the reaction zone from a solvent stock tank 3. The cyclohexane feeding stream 8 from a cyclohexane stock tank 2 and/or from the direct reflux is fed through the reaction zone bottom III into the reaction zone. The oxidation reaction between cyclohexane and the oxidizer of hydrogen peroxide is carried out under the effect of catalyst (in the middle II of the reaction zone), and the part of unreacted cyclohexane is removed from the reaction zone through the reaction zone top. In one embodiment, the part of unreacted cyclohexane is removed from the reaction zone through the reaction zone top in the form of an azeotrope with a part of the water, so as to form a top stream 7. The top stream 7 is fed into a separation tank 4 for the separation between cyclohexane and water, and the separated cyclohexane stream 9 is fed into the cyclohexane stock tank 2; or alternatively, the separated cyclohexane stream 9 is refluxed directly to the reaction zone bottom III and/or is used together with the cyclohexane from the cyclohexane stock tank as the cyclohexane feeding stream 8. The water separated is biochemically treated as waste water, followed by direct discharge. Cyclohexanone and cyclohexanol and the like generated from the reaction as well as the solvent and a part of water (comprising the part of water incorporated with the raw material hydrogen peroxide and the part of water generated from the reaction of hydrogen peroxide) are removed from the reaction zone bottom III, and fed into a solvent separation tank 5. The solvent separated is recycled to the solvent stock tank 3, while the target product of cyclohexanone and/or cyclohexanol as well as a part of water and so on is further fed into a target product separation tank 6 for separation, so as to obtain the target product.

The present invention will be further illustrated by the following examples, whilst the present invention will not be restricted thereto. Without specific indication, the reagents used in the preparation examples and working examples are all chemically pure reagents which are commercially available.

The hollow titanium silicate molecular sieve HTS used in the preparation examples is a commercial product corresponding to the titanium silicate molecular sieve disclosed by CN1301599A (which is a titanium silicate molecular sieve having a MFI structure as measured by X-ray diffraction analysis and is manufactured by Hunan Jianchang Co. Ltd, there being a hysteresis loop between the adsorption isotherm and desorption isotherm for the nitrogen adsorption at low temperature of the molecular sieve, the crystal grain of said titanium silicate molecular sieve having a hollow structure with a radial length of 15-180 nm for the cavity portion of the hollow structure; wherein the adsorption capacity of benzene measured for the molecular sieve under the conditions of 25 degrees C., $P/P_0=0.10$ and 1 h of adsorption time is at least 78 mg/g), with a content of titanium of 2.5 wt %.

The conventional titanium silicate molecular sieve (TS-1) used is a sample of (TS-1) molecular sieve prepared according to the process introduced by page 296, lines 9-24 of the document [Journal of Natural Gas Chemistry 2001, 10(4): 295-307], with a titania content of 2.5 wt %.

The hydrogen peroxide used in examples is each in the form of a 27.5 wt % or 50 wt % of aqueous hydrogen peroxide solution commercially available.

The conventional packing of θ ring used in examples is commercially available from Tianjin Chemtech Co., Ltd., China.

In examples, the various components in the system are analyzed using a vapor phase chromatography and quantified through revised normalization method by referring to the teachings from prior art, based on which the conversion of reactants, the selectivity to product(s) and the effective utility of hydrogen peroxide and the like are calculated for evaluation.

In the examples, the conversion of cyclohexane is calculated as follows:

$$X_{cyclohexane} = \frac{m^\circ_{cyclohexane} - m_{cyclohexane}}{m^\circ_{cyclohexane}} \times 100\%$$

In the examples, the selectivity to the product is calculated as follows:

$$S_{total} = \frac{n_{cyclohexane} + n_{cyclohexanone}}{n^0_{cyclohexane} - n_{cycohexane}} \times 100\%$$

In the examples, the effective utility of hydrogen peroxide is calculated as follows:

$$U_{H_2O_2} = \frac{n_{cyclohexanol} + 2 \times n_{cyclohexanone}}{n^0_{H_2O_2} - n_{H_2O_2}} \times 100\%$$

wherein, X is the conversion; S is the selectivity; U is the effective utility; m is the mass of a component; n is the mole of a component; and wherein m° and n° represent respectively the mass and moles before the reaction.

Preparation Example 1

Under the conditions of atmospheric pressure and 40 degrees C., tetraethyl silicate was added into an aqueous tetrapropyl ammonium hydroxide solution, and stirred for 2 h; then the hollow titanium silicate molecular sieve (HTS) was added and further stirred for 1 h (with a mass ratio among HTS, tetraethyl silicate, tetrapropyl ammonium hydroxide and water of 100:350:5:120). After balling granulation followed by calcination at a temperature of 550 degrees C. for 5 h, a catalyst in the form of microsphere having a diameter of 5 microns was obtained.

Preparation Example 2

The process same as preparation example 1 was repeated, except that the mass ratio among HTS, tetraethyl silicate, tetrapropyl ammonium hydroxide and water was 100:100:10:50, and a catalyst having a diameter of 100 microns was obtained after balling granulation.

Preparation Example 3

The process same as preparation example 1 was repeated, except that the mass ratio among HTS, tetraethyl silicate, tetrapropyl ammonium hydroxide and water was 100:200:40:500, and a catalyst having a diameter of 2000 microns was obtained after balling granulation.

Preparation Example 4

The process same as preparation example 1 was repeated, except that a catalyst having a diameter of 500 microns was obtained after balling granulation.

Preparation Example 5

The process same as preparation example 1 was repeated, except that tetrapropyl ammonium hydroxide was replaced by tetraethyl ammonium hydroxide, and tetraethyl silicate was replaced by tetramethyl silicate.

Preparation Example 6

The process same as preparation example 1 was repeated, except that the mass ratio among HTS, tetraethyl silicate, tetrapropyl ammonium hydroxide and water was 100:300:50:2000.

Preparation Example 7

The process same as preparation example 1 was repeated, except that the hollow titanium silicate molecular sieve (HTS) was replaced by the conventional titanium silicate molecular sieve TS-1.

Example 1

Cyclohexane, hydrogen peroxide solution (with a concentration of 27.5 wt %) and the solvent acetone were fed through the feed inlets of the reaction zone with a mass ratio of 1:1.72:15, wherein the cyclohexane was fed through the second feed inlet, while the hydrogen peroxide solution and the solvent acetone were fed through the first feed inlet. The temperature of the reaction zone was controlled to be 77±3 degrees C. The pressure in the reaction zone was 0.15±0.02 MPa. The space velocity of cyclohexane was $2\,h^{-1}$. The reflux ratio in the reaction zone was 5:1. The plate number of the reaction zone was 35. The plate number between the first feed inlet and the column bottom was 30. The plate number between the second feed inlet and the column bottom was 10. The packing contained 60 wt % of the titanium silicate molecular sieve catalyst obtained according to preparation example 1 and 40 wt % of θ ring. Sample analysis was made after 12 h of stable operation. The conversion of cyclohexane, the selectivity to ketone and alcohol and the effective utility of hydrogen peroxide were listed in table 1.

Example 2

Cyclohexane, hydrogen peroxide solution (with a concentration of 27.5 wt %) and the solvent benzyl cyanide were fed through the feed inlets of the reaction zone with a mass ratio of 1:3.44:8.89, wherein the cyclohexane was fed through the second feed inlet, while the hydrogen peroxide solution and the solvent benzyl cyanide were fed through the first feed inlet. The temperature of the reaction zone was controlled to be 150±5 degrees C. The pressure in the reaction zone was 0.35±0.05 MPa. The space velocity of cyclohexane was $8\,h^{-1}$. The reflux ratio in the reaction zone was 8:1. The plate number of the reaction zone was 35. The plate number between the first feed inlet and the column bottom was 30. The plate number between the second feed inlet and the column bottom was 10. The packing contained 30 wt % of the titanium silicate molecular sieve catalyst obtained according to preparation example 2 and 70 wt % of θ ring. Sample analysis was made after 8 h of stable operation. The conversion of cyclohexane, the selectivity to ketone and alcohol and the effective utility of hydrogen peroxide were listed in table 1.

Example 3

Cyclohexane, hydrogen peroxide solution (with a concentration of 50 wt %) and the solvent tert-butanol were fed through the feed inlets of the reaction zone with a mass ratio of 1:1.72:10, wherein the cyclohexane was fed through the second feed inlet, while the hydrogen peroxide solution and the solvent tert-butanol were fed through the first feed inlet. The temperature of the reaction zone was controlled to be 110±5 degrees C. The pressure in the reaction zone was 0.20±0.02 MPa. The space velocity of cyclohexane was $5\,h^{-1}$. The reflux ratio in the reaction zone was 3:1. The plate number of the reaction zone was 35. The plate number between the first feed inlet and the column bottom was 30. The plate number between the second feed inlet and the column bottom was 10. The packing contained 60 wt % of the titanium silicate molecular sieve catalyst obtained according to preparation example 3 and 40 wt % of θ ring. Sample analysis was made after 18 h of stable operation. The conversion of cyclohexane, the selectivity to ketone and alcohol and the effective utility of hydrogen peroxide were listed in table 1.

Example 4

The process same as example 1 was repeated, except that the titanium silicate molecular sieve catalyst was the titanium silicate molecular sieve shaped catalyst obtained according to the process of preparation example 4.

Example 5

The process same as example 1 was repeated, except that the titanium silicate molecular sieve catalyst was the titanium silicate molecular sieve shaped catalyst obtained according to the process of preparation example 5.

Example 6

The process same as example 1 was repeated, except that the titanium silicate molecular sieve catalyst was the titanium silicate molecular sieve shaped catalyst obtained according to the process of preparation example 6.

Example 7

The process same as example 1 was repeated, except that the titanium silicate molecular sieve catalyst was the titanium silicate molecular sieve shaped catalyst obtained according to the process of preparation example 7.

Example 8

The process same as example 1 was repeated, except that the titanium silicate molecular sieve catalyst was prepared according to a process as follows: mixing HTS and silica sol (having a content of $SiO_2$ of 40 wt %) at a weight ratio of 100:250 and pulping (the slurry therefrom having a solid content of 40 wt %, in which the solid content means the content excluding the moisture from the slurry), and spray granulating to obtain a catalyst in the form of microsphere having a diameter of 50 microns.

Example 9

The process same as example 1 was repeated, except that the solvent was butanone.

Example 10

The process same as example 1 was repeated, except that the solvent was acetic acid.

Example 11

Cyclohexane, hydrogen peroxide solution (with a concentration of 50 wt %) and the solvent water were fed through the feed inlets of the reaction zone with a mass ratio of 2:3:1, wherein the cyclohexane was fed through the second feed inlet, while the hydrogen peroxide solution and the solvent water were fed through the first feed inlet. The temperature of the reaction zone was controlled to be 69±2 degrees C. The pressure in the reaction zone was 0.10±0.02 MPa. The space velocity of cyclohexane was 4 $h^{-1}$. The reflux ratio in the reaction zone was 10:1. The plate number of the reaction zone was 35. The plate number between the first feed inlet and the column bottom was 30. The plate number between the second feed inlet and the column bottom was 10. The packing was 100 wt % of the titanium silicate molecular sieve catalyst obtained according to the process of preparation example 1. Sample analysis was made after 15 h of stable operation. The conversion of cyclohexane, the selectivity to ketone and alcohol and the effective utility of hydrogen peroxide were listed in table 1.

TABLE 1

| Example | Conversion of cyclohexane/% | Selectivity to ketone and alcohol/% | Effective availability of hydrogen peroxide/% |
|---|---|---|---|
| 1 | 65 | 98 | 82 |
| 2 | 63 | 95 | 80 |
| 3 | 67 | 96 | 85 |
| 4 | 60 | 98 | 81 |
| 5 | 54 | 96 | 85 |
| 6 | 49 | 93 | 88 |
| 7 | 38 | 90 | 83 |
| 8 | 44 | 90 | 78 |
| 9 | 52 | 92 | 90 |
| 10 | 50 | 88 | 81 |
| 11 | 72 | 98 | 87 |

It could be seen from table 1 that using the process according to the present invention, the conversion of cyclohexane and the selectivity to ketone and alcohol were both relatively higher, and the availability of hydrogen peroxide was increased greatly by using the preferred shaped catalyst. Meanwhile, as the present invention carried out the reaction in the reaction zone, the heat generated in the oxidation system was used effectively, and energy consumption was saved.

The invention claimed is:

1. A process of oxidizing cyclohexane, comprising feeding cyclohexane, an aqueous hydrogen peroxide solution and optionally an organic solvent into a reaction zone through a feed inlet thereof under the oxidation reaction conditions for contact, and providing all or most of the oxidation product at the reaction zone bottom, wherein a part or all of the packing in the reaction zone is a titanium silicate molecular sieve-containing catalyst in the form of microspheres having a diameter of about 2 to about 5000 microns, and the organic solvent is one or more of an alcohol, a ketone and an organic carboxylic acid having a boiling point of about 40- about 250 degrees C.; wherein the titanium silicate molecular sieve catalyst is prepared by a process comprising:
hydrolyzing an organic silicon compound and an templating agent useful for producing the titanium silicate molecular sieve under hydrolysis conditions to obtain a colloidal solution; then mixing homogeneously the titanium silicate molecular sieve and the colloidal solution to obtain a slurry; and granulating the slurry to obtain the catalyst in the form of microsphere.

2. The process according to claim 1, wherein about 95-about 100 wt % of the oxidation product is obtained from the reaction zone bottom, which product comprises or is selected from the group consisting of cyclohexanone and/or cyclohexanol.

3. The process according to claim 1, wherein the method of feeding cyclohexane, the aqueous hydrogen peroxide solution and the organic solvent into the reaction zone through the feed inlet comprises:
feeding the aqueous hydrogen peroxide solution and the organic solvent into the reaction zone through a first feed inlet, and feeding the cyclohexane into the reaction zone through a second feed inlet;
wherein the plate number or the theoretical plate number between the first feed inlet and the column bottom is of about 50%-about 100% of the total plate number or the total theoretical plate number in the reaction zone; and the plate number or the theoretical plate number between the second feed inlet and the column bottom is of about 10%-about 80% of the total plate number or the total theoretical plate number in the reaction zone.

4. The process according to claim 3, wherein the plate number or the theoretical plate number between the first feed inlet and the column bottom is of about 80%-about 100% of the total plate number or the total theoretical plate number in the reaction zone; and the plate number or the theoretical plate number between the second feed inlet and the column bottom is of about 30%-about 70% of the total plate number or the total theoretical plate number in the reaction zone.

5. The process according to claim 1, wherein the titanium silicate molecular sieve-containing catalyst comprises a carrier and the titanium silicate molecular sieve, and wherein the carrier is used in an amount of about 1-about 90 wt %, and the titanium silicate molecular sieve is used in an amount of about 10-about 99 wt %, based on the total weight of the catalyst.

6. The process according to claim 5, wherein the titanium silicate molecular sieve catalyst is in the form of microspheres having a diameter of about 5 to about 5000 microns.

7. The process according to claim 1, wherein the mass ratio among the titanium silicate molecular sieve, the organic silicon compound, the templating agent useful for producing the titanium silicate molecular sieve and water is about 100:about 10-about 2000:about 2-about 40:about 50-about 1000.

8. The process according to claim 1, wherein the conditions for hydrolysis comprise a hydrolysis period of about 0.5-about 10 h, and a hydrolysis temperature of from room temperature to about 100 degrees C.

9. The process according to claim 1, wherein the templating agent useful for producing the titanium silicate molecular sieve is tetrapropyl ammonium hydroxide and the organic silicon source is tetraethyl silicate.

10. The process according to claim 5, wherein the titanium silicate molecular sieve has a MFI structure, and the crystal grain of the titanium silicate molecular sieve has a hollow structure with a radial length of about 5-about 300 nm for the cavity portion of the hollow structure, wherein the adsorption capacity of benzene measured for the titanium silicate molecular sieve under the conditions of 25° C., $P/P_0=0.10$ and 1 h of adsorption time is at least about 70 mg/g, and there is a hysteresis loop between the adsorption isotherm and desorption isotherm for the nitrogen adsorption at low temperature of the molecular sieve.

11. The process according to claim 1, wherein the packing comprises about 20-about 100 wt % of the titanium silicate molecular sieve-containing catalyst.

12. The process according to claim 1, wherein the mass ratio among cyclohexane, hydrogen peroxide and the organic solvent in the reaction feed is about 1:about 0.03-about 2:about 3-about 15.

13. The process according to claim 1, wherein the organic solvent is one or more of an alcohol, a ketone and a nitrile.

14. The process according to claim 13, wherein the organic solvent is one or more of acetone, methanol, benzyl cyanide and tert-butanol.

15. The process according to claim 1, wherein the conditions for the oxidation reaction comprise a temperature in the reaction zone of about 40-about 200 degrees C., and a reflux ratio of not less than about 2:1.

16. The process according to claim 1, wherein the unreacted cyclohexane and a part of water are remove from the reaction zone through the reaction zone top.

17. A device for carrying out the process according to claim 1, comprising a reaction zone and a separation part, wherein the reaction zone contains a titanium silicate molecular sieve-containing catalyst in the form of microspheres having a diameter of about 2 to about 5000 microns.

18. The device according to claim 17, wherein the reaction zone comprises a top, a middle and a bottom, the top comprising a hydrogen peroxide feed inlet and optionally an organic solvent inlet, the middle being a section in which the oxidation reaction occurs and the bottom comprising a cyclohexane feed inlet.

* * * * *